(12) United States Patent
Marchionini et al.

(10) Patent No.: US 7,595,295 B2
(45) Date of Patent: Sep. 29, 2009

(54) USE OF PLEIOTROPHIN TO PROMOTE NEUROGENERATION

(75) Inventors: Deanna Marchionini, Chicago, IL (US); Timothy Collier, Deerfield, IL (US)

(73) Assignee: Rush University Medical Center, Chicago, IL (US)

( * ) Notice: Subject to any disclaimer, the term of this patent is extended or adjusted under 35 U.S.C. 154(b) by 469 days.

(21) Appl. No.: 11/066,974

(22) Filed: Feb. 25, 2005

(65) Prior Publication Data

US 2006/0193831 A1  Aug. 31, 2006

(51) Int. Cl.
*A61K 38/00* (2006.01)
(52) U.S. Cl. ............... 514/12; 424/93.1; 424/93.7; 435/365; 435/368; 435/377
(58) Field of Classification Search .............. None
See application file for complete search history.

(56) References Cited

U.S. PATENT DOCUMENTS

| 2003/0118556 | A1 | 6/2003 | Kaspar et al. | |
|---|---|---|---|---|
| 2003/0185794 | A1 | 10/2003 | Colley | |
| 2003/0202960 | A1* | 10/2003 | Colley | 424/85.1 |
| 2006/0122116 | A1* | 6/2006 | Hoke et al. | 514/12 |

OTHER PUBLICATIONS

Olson, Nature Med., 2:400-401 (1996).*
Rosenblad et al., Neurosci. 75:979-985 (1996).*
Gash et al., Nature, 380:252-255. (1996).*
Kirik et al., (European Journal of Neuroscience, Nov. 2000, vol. 12 Issue 11, p. 3871-3882.*
Rosenblad et al., Neuroreport 10: 1783-1787(1999).*
Hida et al., NeuroReport 18:179-183, (2007).*
Maier, Irin C. and Schwab, Martin E. Sprouting regeneration and circuit formation in the injured spinal cord: factors and activity. *Phil. Trans. R. Soc. B.*(2006), 361:1611-1634.
Börklund et al. "Towards a neuroprotective gene therapy for Parkinson's disease: use of adenovirus, AAV and lentivirus vectors for gene transfer of GDNF to the nigrostriatal system in the rat Parkinson model" *Brain Research* 886:82-98 (2000).
Bossy-Wetzel et al. "Molecular pathways to neurodegeneration" *Nature Medicine* published online Jul. 1, 2004; doi: 10.1038/nm1067, pp. S2-S9.
Castro et al. "Involvement of Aurora A Kinase during Meiosis I-II Transition in *Xenopus oocytes*" *J. Bio. Chem.* 278:2236-2241 (2003).
Cheetham et al. "Crystal Structure of Aurora-2, an Oncogenic Serine/Threonine Kinase" *J. Bio. Chem.* 277:42419-42422 (2002).
Curtis et al. "Increase cell proliferation and neurogenesis in the adult human Huntington's disease brain" *PANS* 100:9023-9027 (2003).
Dickson et al. "Apoptotic mechanisms in Alzheimer neurofibrillary degeneration: cause or effect?" *J. Clin. Invest.* 114:23-27 (2004).
Barry et al. "Grafted noradrenergic neurons suppress seizure development in kindling-induced epilepsy" *Proc. Natl. Acad. Sci. USA* 84:8712-8715 (1987).
Graeber et al. "Mechanisms of Cell Death in Neurodegenerative Diseases: Fashion, Fiction, and Facts" *Brain Pathol.* 12:385-390 (2002).
Hida et al. "Pleiotrophin exhibits a trophic effect on survival of dopaminergic neurons in vitro" *Eur. J. Neurosci.* 17:2127-2134 (2003).

(Continued)

*Primary Examiner*—David S Romeo
*Assistant Examiner*—Daniel C Gamett
(74) *Attorney, Agent, or Firm*—Foley & Lardner LLP (57) ABSTRACT

The invention provides methods for promoting neuron survival in patients by administering pleiotrophin, or nucleic acids encoding pleiotrophin. Uses of the invention include promoting neuron graft survival, preventing or reducing nervous system degeneration, and restoring the nervous system, in patients suffering from, or at risk for, neurodegenerative disorders.

6 Claims, 4 Drawing Sheets

OTHER PUBLICATIONS

Isacson, Ole "The production and use of cells as therapeutic agents in neurodegenerative diseases" *Neurology* 2:417-424 (2003).

Sakai et al. "MBD3 and HDAC1, Two Components of the NuRD Complex, Are Localized at Aurora-A-positive Centrosomes in M Phase" *J. of Biol. Chem.* 277:48714-48723 (2002).

Warner et al. "Targeting Aurora-2 Kinase in Cancer" *Molecular Cancer Therapeutics* 2:589-595, 2003.

Vila et al. "Targeting Programmed Cell Death in Neurodegenerative Diseases" *Neuroscience* 4:1-11 (2003).

DeKosky et al. "Looking Backward to Move Forward: Early Detection of Neurodegenerative Disorders" *Science* 302:830-834, 2003.

Giménez y Ribotta, M. "Gene therapy strategies in neurodegenerative diseases" *Histol Histopathol* 16:883-893 (2001).

Salcedo et al. "Differential expression and responsiveness of chemokine receptors (CXCR1-3) by human microvascular endothelial cells and umbilical vein endothelial cells" *The FASEB Journal* 14:2055-2064 (2000).

Jones et al. "The chemokine receptor CXCR3 is expressed in a subset of B-cell lymphomas and is a marker of B-cell chronic lymphocytic leukemia" *Blood* 95:627-632 (2000).

Reinhart et al. "Increased expression of the inflammatory chemokine CXC chemokine ligand 9/monokine induced by interferon-y in lymphoid tissues of rhesus macaques during simian immunodeficiency virus infection and acquired immunodeficiency syndrome" *Blood* 99:3119-3128 (2002).

Gangur et al. "Human IP-10 selectivity promotes dominance of polyclonally activated and environmental antigen-driven IFN-y over IL-4 responses" *The FASEB Journal* 12:705-713 (1998).

Sauty et al. "The T Cell-Specific CXC Chemokines IP-10, Mig, and I-TAC Are Expressed by Activated Human Bronchial Epithelial Cells" *J. of Immunology* 162-3549-3558 (1999).

Cole et al. "Interferon-inducible T Cell Alpha Chemoattractant (I-TAC): A Novel Non-ELR CXC Chemokine with Potent Activity on Activated T Cells through Selective High Affinity Binding to CXCR3" *J. Ex. Med.* 187:2009-2021 (1998).

Qin et al. "The Chemokine Receptors CXCR3 and CCR5 Mark Subsets of T Cells Associated with Certain Inflammatory Reactions" *J. Clin. Invest.* 101:746-754 (1998).

Lu et al. "Structure and function of the murine chemokine receptor CXCR3" *Eur. J. Immunol.* 29:3804-3812 (1999).

Lalor, et al. "Recruitment of lymphocytes to the human liver" *Immunol. Cell Biol.* 80:52-64 (2002).

Andus et al. "Cytokines and the liver in health and disease. Effects on liver metabolism and fibrogenesis" *Acta Gastroenterol Belg.* 57:236-244 (1994).

Nakao et al. "Lazaroids improve the survival of grafted rat embryonic dopamine neurons" *Proc. Natl. Acad. Sci. USA* 91:12408-12412 (1994).

Dunnett et al. "Basic neural transplantation techniques. I. Dissociated cell suspension grafts of embryonic ventral mesencephalon in the adult rat brain" *Brain Research Protocols* 1:91-99 (1997).

\* cited by examiner

USE OF PLEIOTROPHIN TO PROMOTE NEUROGENERATION

FIELD OF THE INVENTION

The invention provides methods for promoting neuron survival in a patient by administering pleiotrophin, or nucleic acids encoding pleiotrophin, to tissues of the brain. Uses of the invention include promoting neuron graft survival, preventing or reducing neurodegeneration, and restoring nervous system function.

BACKGROUND OF THE INVENTION

The World Health Organization predicts the number of people suffering from some form of neurodegenerative disorder to approach 29 million by the year 2020. Such neurodegenerative disorders include Parkinson's disease (PD), Huntington's disease (HD), Alzheimer's disease (AD), vascular dementia, and other disorders. While the etiology of theses disorders varies, the end result is the loss of neurons, which leads to cognitive and/or motor skill dysfunction, and eventually death.

Current treatments to improve the quality of life for afflicted individuals involve the administration of dopamine agonists or L-dopa. However, protracted administration of these drugs leads to decreased response and decreased treatment efficacy. While infusion of trophic factors, such as glial cell line-derived neurotrophic factor (GDNF), has been proposed for treating and/or modulating the progression of neurodegenerarative disorders, it has yet to provide clinical benefits to patients.

The transplantation of healthy cells into tissues of the nigrostriatal system has also been proposed to treat PD and other neurodegenerative disorders; however, survival rate of transplanted embryonic tissues is low (e.g., 5-10% for embryonic ventral mesencephalon (VM) tissue) and the grafts have limited capacity to reinnervate the affected tissues, such as the striatum. The transplantation of stem cells faces similar challenges, in addition to difficulties associated with maintaining desired cell phenotypes.

The treatment of neurodegerative disorders and the management of patients suffering from such disorders imposes a high burden on private and public health care systems, caregivers, and family members. Current therapies are unable to effectively prevent the onset of these disorders or arrest their progression. A need clearly exists for effective treatments for neurodegenerative disorders.

SUMMARY OF THE INVENTION

One embodiment of the invention provides a method for promoting neuron graft survival in a patient. Such neuron grafts include dopamine neurons. The method comprises administering to a patient receiving a graft an amount of pleiotrophin suitable for promoting survival of the graft. The composition comprising pleiotrophin may be administered to the patient prior to, contemporary with, or following graft transplantation. In one embodiment of the invention, the neuron graft comprises neuronal cells or neuron precursor cells, which may include but are not limited to dopamine neurons, stem cells, or other neuron progenitor cells.

Another embodiment of the invention provides a method for preventing or reducing neurodegeneration in a patient comprising administering to the patient an amount of pleiotrophin suitable for preventing or reducing neurodegeneration. Neurodegeneration includes but is not limited to cerebral degeneration, dopaminergic nigrostriatal system degeneration, cortical degeneration, spinal cord degeneration, cerebellar degeneration, hippocampal degeneration and degeneration involving the basal ganglia.

Yet another embodiment of the invention provides a method for restoring the nervous system, i.e., promoting neuroregeneration, in a patient, the method comprising administering to the patient a composition comprising an amount of pleiotrophin suitable for restoring the nervous system.

In some embodiments of the invention, neurons of the nigrostriatal system are biological targets for the methods described herein. In other embodiments, the tissues or regions of the brain to which pleiotrophin is administered or targeted include but are not limited to the cerebrum, striatum, substantia nigra, cortex, cerebellum, hippocampus, basal forebrain, basal ganglia, and spinal cord.

The methods of the invention include the administration of pleiotrophin polypeptides and/or polynucleotides encoding pleiotrophin. In addition, pleiotrophin may be administered along with other beneficial compositions, including neurotrophic factors, In a particular embodiment of the invention, the trophic factor is glial cell line-derived neurotrophic factor (GDNF).

DETAILED DESCRIPTION OF THE INVENTION

Figure 1:
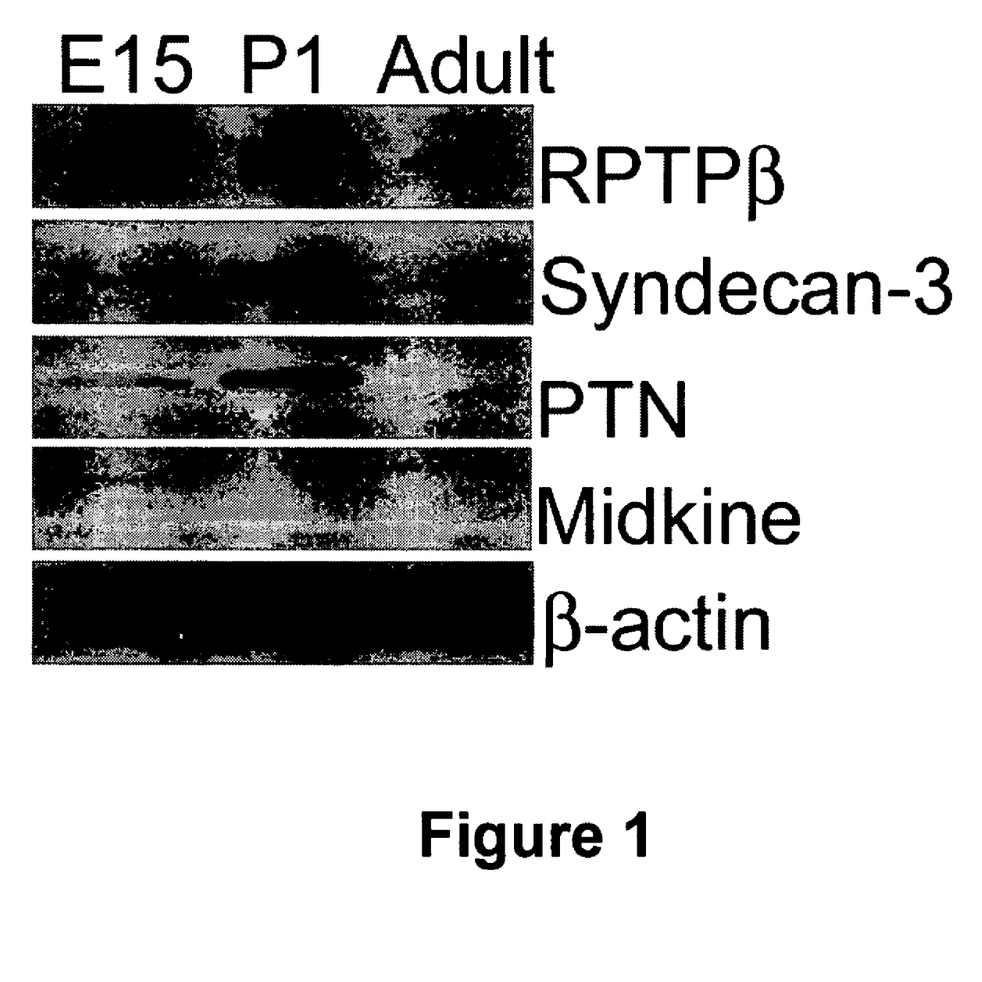
FIG. 1. Results of immunoblot analyses showing that pleiotrophin is most highly expressed in the striatum at P1 and down-regulated by adulthood and that the pleiotrophin receptor, RPTP $\beta/\zeta$, is most highly expressed during the E15 and P1 stages of nigrostriatal development, and down-regulated in adulthood. Syndecan-3 is expressed in the striatum at all three time points. E15, embryonic day 15; P1, postnatal day 1; Adult, adult animals.
Figure 2:
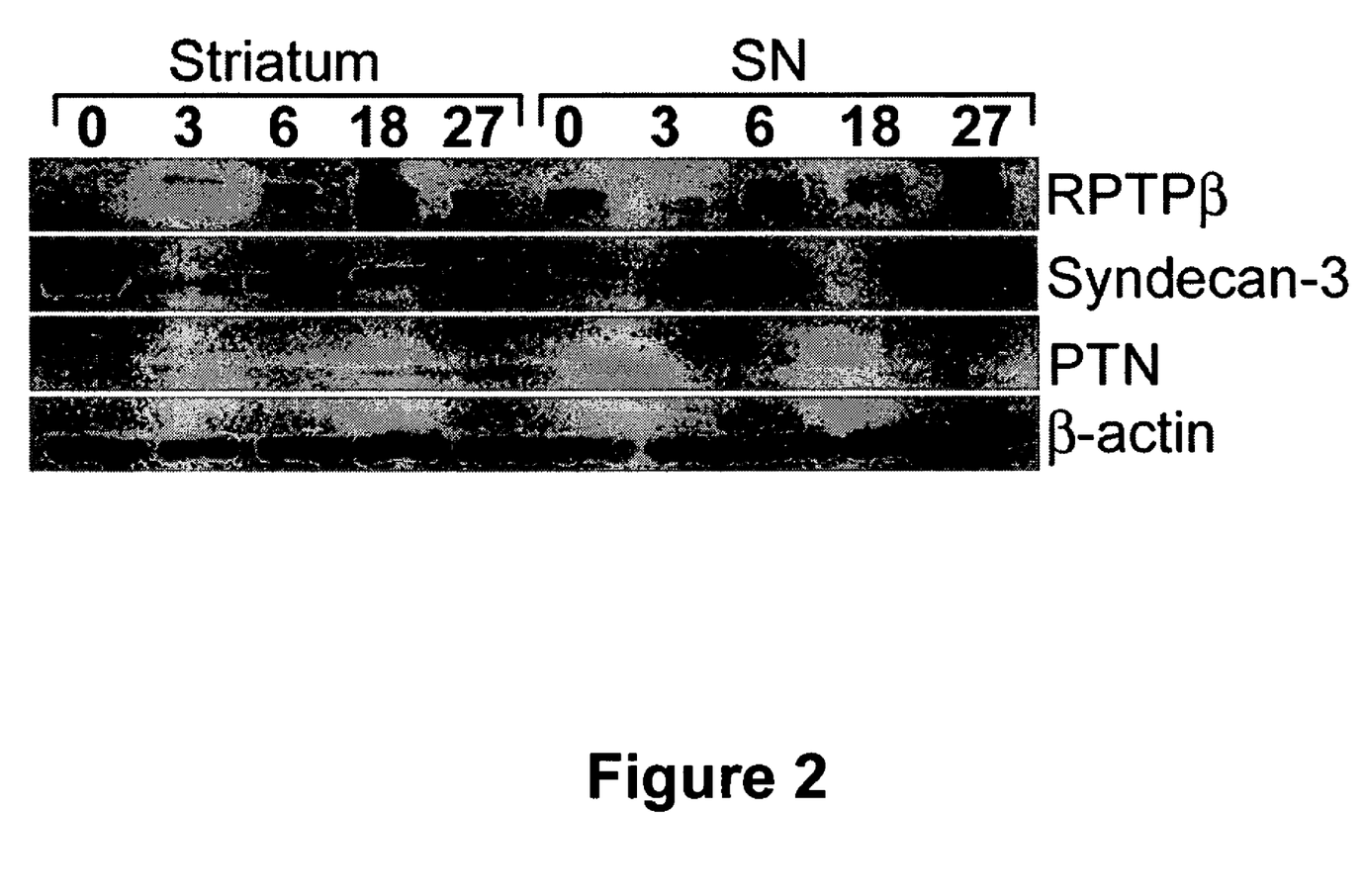
FIG. 2. Results of immunoblot analyses showing that pleiotrophin is upregulated in the striatum, but not substantia nigra (SN), following dopaminergic denervation using 6-OHDA; that RPTP $\beta/\zeta$ is upregulated in the striatum after dopaminergic denervation; and that Syndecan-3 is transiently down-regulated in the striatum after dopaminergic denervation. Numbers indicate days following 6-OHDA administration.

The invention was based, in part, on the observation that both pleiotrophin, and its receptor, RPTPβ/ζ, are highly expressed in the striatum of rat brains during nigrostriatal development, with high levels being detected at P1 (FIG. 1). The expression in the striatum of pleiotrophin and RPTPβ/ζ are also upregulated following 6-hydroxydopamine (6-OHDA)-dopaminergic denervation, with expression returning to pre-injury levels (FIG. 2).

Pleiotrophin is a member of a family of heparin-binding growth differentiation factors that is expressed by, e.g., axons, radial glial fibers, reactive astrocytes, and during development in cells of the axonal tracts. Pleiotrophin has trophic effects on numerous cell populations, and appears to be an important ligand for initiating the signaling cascade to promote neurite outgrowth. At least four pleiotrophin receptors have been identified, namely (i) syndecan-3, (ii) anaplastic lymphoma kinase, (iii) low-density lipoprotein receptor-related protein, and (iv) RPTPβ/ζ.

Without being limited to a theory, the invention is based, in part, on the observation that polypeptides that are highly expressed in the developing mammalian brain, or highly expressed in the mammalian brain in response to injury, will promote the survival of neurons in the brains of patients with a neurodegenerative disorder.

In particular, the invention provides methods for using pleiotrophin to prevent and/or treat neurodegenerative disorders by protecting and/or restorating endogenous neurons and/or neuronal tissue grafts in the brains of patients at risk for and/or suffering from one or more neurodegenerative disorders, including but not limited to Parkinson's disease (PD), Alzheimer's disease, Huntington's disease, and other neurodegenerative disorder, some of which are discussed above and/or below.

The invention also provides methods of using pleiotrophin to treat neurodegenerative disorders, via one or more of several different therapeutic approaches, with the goal of infusing or delivering the pleiotrophin polypeptide, alone or in combination with other trophic factors, to the site or sites of neurodegenration in a patient's brain.

In one aspect of the invention, pleiotrophin polypeptides, or polynucleotides encoding pleiotrophin polypeptides, are infused into the striatum of a patient, prior to, accompanying, or following transplantation of embryonic dopamine cells, with the goal of promoting homogenous reinnervation of the striatum. Incomplete innervation of, for example, the striatum, has been hypothesized to contribute to graft-derived dyskinesias in Parkinson's patients. The infusion of pleiotrophin, in conjunction with a dopamine neuron graft, will contribute to reinnervation of the striatum and ameliorate the functional deficits in patients suffering from neurodegenerative disease, including those identified herein.

In another aspect of the invention, pleiotrophin polypeptides, or polynucleotides encoding pleiotrophin polypeptides, are infused into the brain of a patient, for example, the striatum or substantia nigra, to protect the dopaminergic nigrostriatal system from neurodegeneration, such as Parkinson's-induced degeneration. This therapy is particularly useful for treating early-stage Parkinson's disease, i.e., before or soon after the patient displays the cognitive and motor function symptoms characteristic of the disease.

In another aspect of the invention, pleiotrophin polypeptides, or polynucleotides encoding pleiotrophin polypeptides, are infused into the brain of a patient, for example, the striatum or substantia nigra, to restore the dopaminergic nigrostriatal system, following neurodegeneration. This therapy is particularly useful for treating late-stage Parkinson's disease, i.e., once the patient clearly displays the cognitive and motor function symptoms characteristic of the disease.

The invention includes various methods of infusing pleiotrophin into the brains of patients suffering from neurodegenerative disorders. In one embodiment of the invention, the invention includes infusing pleiotrophin polypeptides, including modified polypeptides, into the brain.

Pleiotrophin polypeptides for administration to a patient may be isolated from mammals, including humans, or expressed and isolated from a heterologous host organism, such as bacteria, yeast, or cultured cells, including but not limited to insect, mammalian, primate, and human cells. Methods for isolating, expressing, and purifying polypeptides are well-known in the art and do not constitute part of the invention.

It may be desirable to infuse the native pleiotrophin polypeptide or a fragment or variant thereof, provided that the fragment or variant possesses pleiotrophin activity. Fragments or variants may also be more readily expressed, purified, and/or isolated than the native (i.e., naturally occurring) pleiotrophin polypeptide, affording particular advantages over the use of native pleiotrophin. Alternatively or additionally, fragments or variants may be more stable, or even more active, than the native pleiotrophin polypeptide, affording additional advantages over the use of native pleiotrophin. Accordingly, as used herein, fragments and/or variants of pleiotrophin, having the activity of pleiotrophin, may be substituted in any of the above or following embodiments of the invention, without an explicit statement to that effect.

For long term expression, to avoid the need to express, isolate, and/or purify pleiotrophin, or to facilitate the expression of pleiotrophin in a subset of cells at the site of delivery, polynucleotides encoding pleiotrophin may be used in practicing the invention. Such polynucleotides include viral vectors and other expression vectors.

Viral vectors for use in gene delivery include but are not limited to, retrovirus vectors (including lentivirus vectors), adenovirus vectors, adeno-associated virus vectors, herpesvirus vectors, and poxvirus vectors. Many other viruses have been shown to be capable of expressing genes-of-interest in cells, and the construction of such recombinant viral vectors does not constitute part of the invention.

Criteria for selecting viral vectors include but are not limited to, the cell-type-specificity of the virus; the level of expression desired and the level of expression possible using a particular virus vector; the tendency of a particular viral vector to cause lysis, apoptosis, or other forms of cell death; ease of production of sufficient quantities and qualities of viral vector; the extent of immune response to a particular viral vector, which may also vary among patients; and the relative abilities of particular viral vectors to produce properly folded, post-translationally-modified, and active pleiotrophin. Viral vectors, as well as many of the advantages and disadvantages of particular viral vectors, are well-known in the art and do not constitute part of the invention.

In addition to viral vectors, non-viral expression vectors may also be used to infuse pleiotrophin into to the brains of patients. Almost any eukaryotic expression vector, including commercially available expression vectors, is suitable for this purpose, provided that it directs the expression of pleiotrophin in sufficient quantities and in an appropriate cell-type-specific manner (e.g., by using an appropriate promoter and/or enhancer elements). Methods for delivering expression vectors to brain tissues include but are not limited to direct naked DNA delivery, liposome-mediated delivery, ballistic DNA delivery, and other means of causing DNA to be taken up by cells. Such methods are known in the art and do not constitute part of the invention.

Pleiotrophin polypeptides or polynucleotides encoding pleiotrophin may be administered to one or more tissues in brain. Such tissues include but are not limited to cerebrum, striatum, substantia nigra, cortex, hippocampus, basal forebrain, spinal cord, and support structures, thereof. Particular tissues include the striatum and the substantia nigra.

The amount of pleiotrophin to be administered to a patient depends on numerous factors, including the severity of the disease and/or the age and physical condition of the patient. As a starting point, the amount of pleiotrophin polypeptide to be delivered to a patient is between about 10 ng to about 500

µg; however, amounts outside this range are within the scope of the invention. Examples of amounts within this range include but are not limited to 10, 50, 100, or 250 ng and 0.5, 1, 5, 10, 50, 100, and 250 µg.

The amount of polynucleotide encoding pleiotrophin to be administered will depend on additional parameters, including but not limited to promoter efficiency, efficiency of DNA uptake by cells, efficiency of infection with viral vectors, and longevity of expression. Experience with the particular vector selected for use in practicing the invention, which can be found in the relevant literature, will assist in determining a starting amount of the nucleotide to be administered.

According to any of the methods of the invention, pleiotrophin may be administered in combination with one or more additional trophic factors, including neurotrophic factors, which include but are not limited to GDNF. As a starting point, the amount of GDNF polypeptide to be delivered to a patient is between about 10 ng to about 500 µg, although amounts outside this range are within the scope of the invention. Examples of amounts within this range include those identified above, with respect to pleiotrophin. The amount of polynucleotide encoding such additional trophic factors will depend on additional parameters, also as discussed, above.

The methods of the instant invention are useful for treating, preventing, and or reversing the progress of a variety of neurodegenerative disorders, including but not limited to Parkinson's disease, Huntington's disease, and Alzheimer's disease. Other neurodegenerative diseases can be treated, provided that the basis of the disease is neurodegeneration such that the infusion of pleiotrophin can arrest or prevent degeneration and/or can restore tissue following neurodeneration.

In addition to Parkinson's disease, Huntington's disease, and Alzheimer's disease, other diseases that can be treated by the methods of the instant invention include but are not limited to, the vascular dimentias, which are usually caused by brain damage from cerebrovascular or cardiovascular events, such as stroke, but may also be associated with genetic disorders, such as endocarditis or amyloid angiopathy. Vascular dementias include, multi-infarct dementia (MID); Binswanger's disease; and cerebral autosomal dominant arteriopathy with subcortical infarct and leukoencephalopathy (CADASIL). Vascular dementia may also be caused by vasculitis, hypotension, lesions resulting from brain hemorrhage, lupus erythematosus, and temporal arteritis.

Additional examples of diseases that can be treated by the methods of the instant invention include, but are not limited to, amyotrophic lateral sclerosis; Lewy body dementia (also called frontal lobe dementia, which includes Pick's disease and primary progressive aphasia); dementia pugilistica (also called traumatic encephalopathy or Boxer's syndrome); post-traumatic dementia; corticobasal degeneration; Creutzfeldt-Jakob disease; Niemann-Pick disease; Batten disease; and Lafora body disease. This list is not intended to be exhaustive and other neurodegenerative disorders can also be treated or prevented using the methods described, herein, and modifications of the methods, which will be apparent to those skilled in the art.

The following Examples illustrate some of the findings leading to the invention and the application of the invention in an animal model. These Examples should in no way be construed to limit the invention.

EXAMPLES

Unless otherwise specified, the following terms have the following meanings. Other scientific terms that are not defined, herein, are to be given there usual meaning in the art.
DA dopamine
GDNF glial cell line-derived neurotrophic factor
Tris-HCl tris(hydroxymethyl)aminomethane hydrochloride
NaCl sodium chloride
NP-40 Nonidet P-40
EDTA ethylenediamine tetraacetic acid
PMSF phenylmethylsulfonylfluoride
SDS sodium dodecyl sulfate
VM ventral mesencephalon
LGE lateral ganglionic eminence
CMF calcium-magnesium-free buffer
PFA paraformaldehyde
PBS phosphate-buffered saline
TBS Tris-buffered saline
DIV 4 fourth-day of cell culture
HSSF hormone-supplemented serum free medium
DAB 3,3-diaminobenzidine
E14 embryonic day 14
P1 postnatal day 1
i.p. intraperitoneal
6-OHDA 6-hydroxydopamine
SN substantia nigra
DAergic dopaminergic Example 1

Identification of Proteins Expressed During Nigrostriatal Development

Animals and Sample Preparation:

Rats used in the experiment were purchased from Harlan (Indianapolis, Ind., USA) and housed in the vivarium at Rush University Medical Center. The Animals were euthanized by $CO_2$ inhalation, followed by rapid decapitation. Fisher 344 rat post-natal day 1 (P1) and adult striata were dissected on ice and pooled. Timed pregnant Fisher 344 rats provided embryonic day 14 or 15 (E14 or E15) pups, from which the lateral ganglionic eminence (LGE) or ventral mesencephalon (VM) were dissected according to Nakao et al. (1994) and Dunnett and Björklund (1997). All tissues were collected in calcium-magnesium-free buffer (CMF), for culture studies.

Immunoblot Analysis:

For immunoblot analysis, tissues were homogenized in ice cold Lysis buffer (0.1 M Tris, 0.9% NaCl, 0.5% NP-40, 1 mM EDTA, 0.01 M aprotinin, 0.5 mM leupeptin, 0.7 mM pepstatin, and 2 mM PMSF). The protein concentration in the sample was determined using the Lowry assay.

20 µg each total protein was denatured in Laemmli sample buffer with 2% 2-mercaptoethanol, then subjected to electrophoresis on a 4-20% gradient SDS-polyacrylamide gel. The resolved proteins were then transferred to nitrocellulose membrane for immunoblot analysis. Nonspecific binding was blocked using 5% non-fat dried milk in Tris-buffered saline (TBS) with Tween 20 (50 mM Tris-HCl, 200 mM NaCl, and 0.05% Tween 20). The blocked membranes were incubated for about 12 hours at 4° C. with antibodies specific for (i) midkine (0.1 µg/ml; R&D Systems, Minneapolis, Minn.), pleiotrophin (0.1 µg/ml; R&D Systems), RPTPβ/ζ (1:250; BD Biosciences, San Diego, Calif.), syndecan-3 (1:150; Zymed, South San Francisco, Calif.), or β-actin as a loading control (1:5000; Abcam, Cambridge, Mass.). Membranes were incubated for about one hour at room temperature in horse radish peroxidase-conjugated donkey anti-goat, goat anti-mouse, or goat anti-rabbit antibody (1:5000). The membranes were then developed by chemiluminescence. All immunoblot analyses were repeated three times with independent samples.

Results:

Immunoblot analyses revealed that pleiotrophin was highly expressed in the striatum during nigrostriatal development. With respect to the time points tested, peak expression was at P1 and significant down-regulation was observed in adulthood (FIG. 1). The expression of the pleiotrophin receptor, RPTPβ/ζ, was also elevated in developing tissues, with high levels being detected at P1. Syndecan-3 appears to be expressed at similar levels in the striatum throughout nigrostriatal development.

Both RPTPβ/ζ and syndecan-3 were observed in the developing SN, with RPTPβ/ζ being localized to DA neurons (data not shown).

These results indicate that the expression of pleiotrophin, and its receptor, RPTPβ/ζ, is significantly upregulated during nigrostriatal development, suggesting that these proteins play an important role in nigrostriatal development.

Example 2

Identification of Proteins Expressed Following Dopaminergic Denervation

Animals and Sample Preparation:

Animal treatment and sample preparation were as described in Example 1.

Dopaminergic Denervation:

Anesthetized (30 mg/kg pentobarbital, intraperitoneal; i.p.) 3-month-old male Fisher 344 rats (n=15) received stereotaxic injections of 6-hydroxydopamine (5.0 µg/µl; 6-OHDA) into the medial forebrain bundle (AP −4.3, ML +1.2, DV −7.5) and SN pars compacta (AP −4.8, ML +1.5, DV −7.5; Paxinos and Watson, 1986) at a rate of 1 µl/min for 2 minutes. Deeply anesthetized (50 mg/kg pentobarbital; i.p.) animals were saline perfused at 0, 3, 6, 18 and 27 days following administration of 6-OHDA. Each group consisted of 3 animals. Brains were removed and the lesioned striatum and SN were dissected on ice and prepared for immunoblot analysis, as above.

Immunoblot Analysis:

Immunoblot analysis was performed as in Example 1.

Results:

Immunoblot analyses revealed that both pleiotrophin and RPTPβ/ζ were upregulated in the striatum and SN following DAergic denervation; (FIG. 2). By contrast, Syndecan-3 was transiently down-regulated in the striatum and SN after DAergic denervation, but returned to pre-injury expression levels.

These results indicated that the expression of pleiotrophin, and its receptor, RPTPβ/ζ, are significantly upregulated following dopaminergic denervation by 6-OHDA, which is a model of the neurodegereration seen in Parkinson's disease. The results suggest that administration of pleiotrophin and/or RPTPβ/ζ, to tissues associated with dopaminergic denervation, will enhance or restore the brain's neuroregenerative capacity.

Example 3

Effects of Pleiotrophin and GDNF on Tyrosine Hydroxylase Immunoreactive Neurons and Neurite Length in the Developing Nigra Cell Culture Analysis:

VM tissue, in CMF buffer, was rinsed several times in additional CMF buffer, then incubated in hormone-supplemented serum free medium (HSSF; equal volumes of DMEM and Ham's F-12 supplemented with 1.0 mM glutamine, 1.0 mg/ml bovine albumin fraction V, 0.1 mg/ml apo-transferrin, 5 µg/ml insulin, 10 nM L-thyroxin, 20 nM progesterone, 30 nM sodium selenite, 10 U/ml penicillin, and 2.5 µg/ml fungizone) with 0.125% trypsin for about 10 minutes at 37° C. After several rinses with CMF, followed by HSSF/0.004% DNase, cells were dissociated into a single cell suspensions by trituration through a fire-polished Pasteur pipette. The cells were counted with a hemocytometer and verified to be greater than 95% viable using the trypan blue exclusion test.

To evaluate the effects of trophic factors on VM cultures, VM cells were dry plated into 30,000 cell microislands on poly-D-lysine coated plates. After about 1 hour at 37° C., the wells were flooded with HSSF containing 0, 10, 50, 100 or 250 ng/ml trophic factor (i.e., pleiotrophin, midkine or GDNF), or 100 ng/ml heat-inactivated pleiotrophin, as a control. The cells were fixed on DIV 4. The fixed cells were incubated in tyrosine hydroxylase (TH)-specific antibody (1:4000; Chemicon, Temecula, Calif.) for about 12 hours at 4° C. Following TBS rinses, the fixed cells were incubated for about 2 hours in biotinylated goat anti-mouse IgG antibody (1:400, Chemicon), rinsed again, and incubated for about another 2 hours in avidin-biotin-peroxidase complex reagent (Vector, Burlingame, Calif.). TH immunoreactivity was visualized using the chromagen 3,3-diaminobenzidine (DAB) with 0.03% hydrogen peroxide. Neuronal cells identified with the TH-specific antibody were counted in each of nine 20× fields at the center of each well, added, and used for statistical analysis. The center of each well was also digitally captured and analyzed using Image Analysis Software (SigmaScan Pro). TH immunoreactive neuronal cells in the field of view were measured, and the average cell length, for each well, was used for statistical analysis. Each experiment consisted of at least 4 wells per treatment, and each experiment was repeated at least twice.

Figure 3:
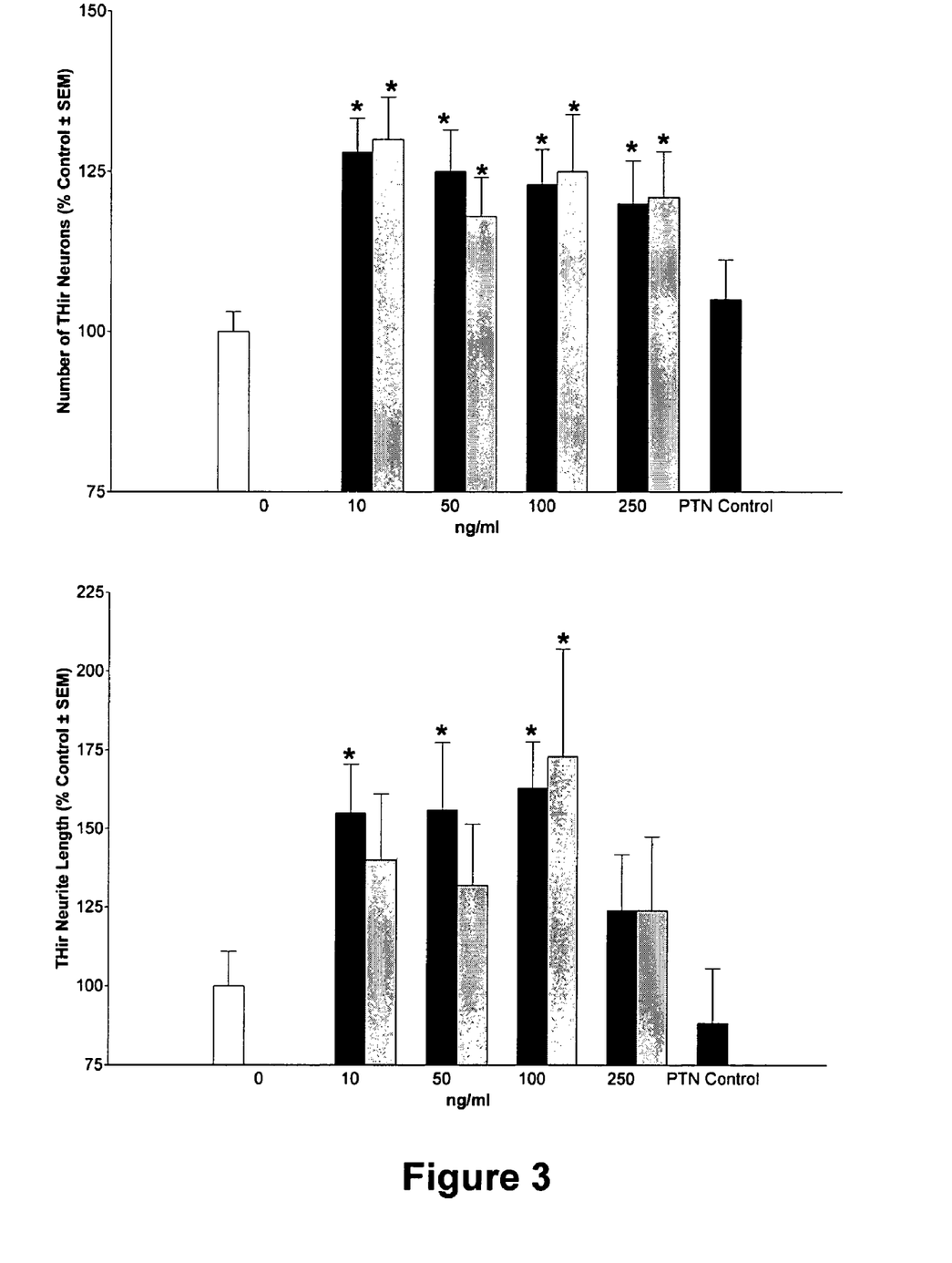
FIG. 3. Graphs showing the number of tyrosine hydroxylase immunoreactive (THir) neurons (upper panel) and neurite length (lower panel) following the treatment of ventral mesencephlic tissue with 0, 10, 50, 100 or 250 ng/ml pleiotrophin (black bars) or GDNF (grey bars), or 100 ng/ml heat-inactivated pleiotrophin as a control.

Results:

The addition of pleiotrophin or GDNF to E14 VM cultures significantly increased the number of tyrosine hydroxylase immunoreactive (THir) neurons relative to control cells receiving no trophic factors (FIG. 3, upper panel). The expression of tyrosine hydroxylase is a well-known marker used for identifying dopaminergic neurons. Specifically, the addition of 10, 50 or 100 ng/ml pleiotrophin increased the number of THir neurons to 128%±5.3%, 125%±6.5% and 123%±5.5% of control, respectively (black bars; $p<0.01$). The addition of heat inactivated pleiotrophin resulted in no change in the number of THir neurons (105%±6.2% of control; $p>0.05$). The addition of 10, 50 or 100 ng/ml GDNF also produced a comparable in crease increase in the number of THir neurons to 130%±6.6%, 118%±6.1% and 125%±8.9% of control, respectively (grey bars; $p<0.05$).

The addition of pleiotrophin or GDNF to E14 VM cultures also significantly increased the neurite length of THir cells (FIG. 3, lower panel). Specifically, the addition of 10, 50 or 100 ng/ml pleiotrophin increased neurite length by 155%±15.5%, 156%±21.5%, 163%±14.7% of control, respectively (black bars; $p<0.03$). The addition of heat-inactivated pleiotrophin did not promote THir neurite outgrowth (88%±17.2% of control; $p>0.05$). The addition of 100 ng/ml GDNF resulted in a 173%±34% of control increase in THir neurite length ($3^{rd}$ grey bar; $p<0.02$). The addition of 10 or 50 ng/ml GDNF did not result in significant effects on TH immunoreactive neurite outgrowth ($1^{st}$ and $2^{nd}$ grey bars; $p>0.05$).

Based on these results, pleiotrophin exerted trophic effects at lower doses than GDNF; however, both neurotrophic factors provided a dopaminergic response.

Figure 4:
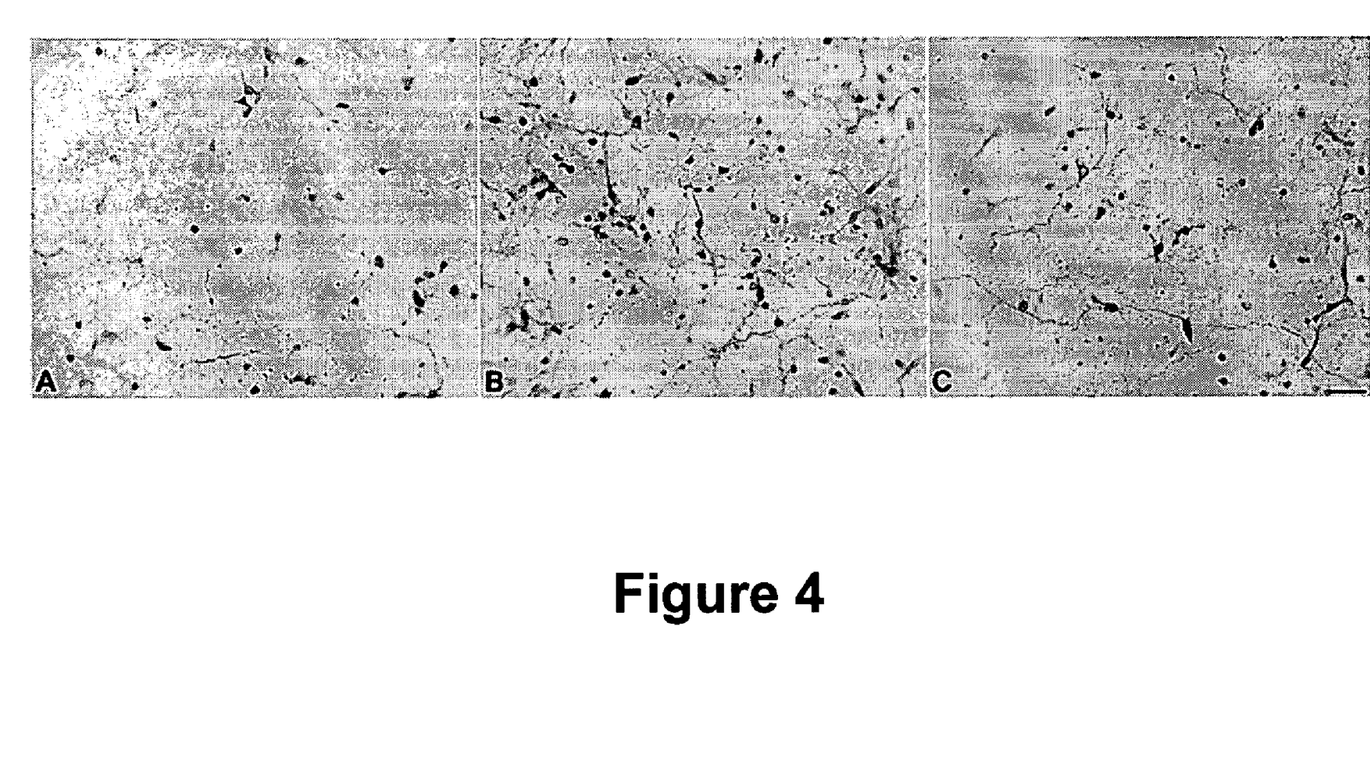
FIG. 4. Photomicrographs showing the morphology of untreated DA neurons (A) and DA neurons treated with 100 ng/ml pleiotrophin (B) or GDNF (C).

Photomicrographs (FIG. 4) showed distinct morphological changes in DA neurons treated with 100 ng/ml pleiotrophin (B) or GDNF (C), compared to untreated DA neurons (A), consistent with the results obtained in the THir analysis.

The above examples are provided to illustrate the methods of the invention and should in no way be construed as limiting. Related methods and uses of the invention will be apparent to one skilled in the art upon reading the specification.

What is claimed is:

1. A method for promoting dopaminergic neuron graft survival and reinnervation of the tissues of the brain in a patient suffering from Parkinson's disease comprising administering to the striatum or substantia nigra of the patient an amount of pleiotrophin suitable for promoting graft survival and reinnervation, wherein said amount of pleiotrophin promotes reinnervation of the tissues of the brain and survival of dopaminergic neuron grafts administered to the patient.

2. The method of claim 1, wherein the amount of pleiotrophin is administered to the patient prior to neuron graft transplantation.

3. The method of claim 1, additionally comprising administering an amount of GDNF to the patient.

4. The method of claim 1, wherein the Parkinson's disease is early stage Parkinson's disease.

5. The method of claim 1, wherein the pleiotrophin is administered contemporaneously with graft transplantation.

6. The method of claim 1, wherein the pleiotrophin is administered following graft transplantation.

* * * * *

UNITED STATES PATENT AND TRADEMARK OFFICE
CERTIFICATE OF CORRECTION

| | |
|---|---|
| PATENT NO. | : 7,595,295 B2 |
| APPLICATION NO. | : 11/066974 |
| DATED | : September 29, 2009 |
| INVENTOR(S) | : Marchionini et al. |

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 469 days Delete the phrase "by 469 days" and insert -- by 892 days --

Signed and Sealed this

Fourth Day of May, 2010

David J. Kappos
*Director of the United States Patent and Trademark Office*